(12) United States Patent
Huh

(10) Patent No.: US 7,462,806 B2
(45) Date of Patent: *Dec. 9, 2008

(54) DAZZLE PREVENTION DEVICE HAVING ELECTRO MAGNETIC WAVE DETECTION FUNCTION AND DETECTION MODE SELECTION

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 388 days.

This patent is subject to a terminal disclaimer.

(21) Appl. No.: 10/565,858

(22) PCT Filed: Jan. 4, 2005

(86) PCT No.: PCT/KR2005/000005

§ 371 (c)(1),
(2), (4) Date: Jan. 25, 2006

(87) PCT Pub. No.: WO2005/092263

PCT Pub. Date: Oct. 6, 2005

(65) Prior Publication Data

US 2008/0120752 A1    May 29, 2008

(30) Foreign Application Priority Data

Mar. 26, 2004  (KR) ...................... 10-2004-0020731
Jul. 6, 2004    (KR) ...................... 10-2004-0052291

(51) Int. Cl.
*G01J 1/32* (2006.01)
(52) U.S. Cl. .................................. 250/205; 250/214 D
(58) Field of Classification Search ................. 250/216, 250/205, 201.1, 214 D, 554; 219/130.1–130.5; 359/265, 601–604

See application file for complete search history.

(56) References Cited

U.S. PATENT DOCUMENTS

RE29,684 E  *  6/1978  Gordon (Continued)

FOREIGN PATENT DOCUMENTS

KR    2000-0043613    7/2000

(Continued)

OTHER PUBLICATIONS

PCT Written Opinion of the International Searching Authority; International Application No. PCT/KR2005/000005; International filing date: Jan. 4, 2005; Date of Mailing: Apr. 27, 2005.

(Continued)

*Primary Examiner*—Que T Le
(74) *Attorney, Agent, or Firm*—Cantor Colburn LLP

(57) ABSTRACT

A dazzle prevention device having an electromagnetic wave detection function is disclosed. The device includes an optical detection means, an electromagnetic wave sensor means, the electromagnetic wave detection means, a control means, and a light transmission control means. The optical detection means detects light generated from the welding or cutting torch. The electromagnetic wave sensor means detects an electromagnetic wave. The electromagnetic wave detection means compares a signal, which is input through the electromagnetic wave sensor means and resonated, with a variably set reference value. The control means applies the electromagnetic wave detection mean drive signal to the electromagnetic wave detection means and monitors the variation of an electromagnetic signal using the output of the electromagnetic wave detection means. The light transmission control means controls the variation of light transmittance of the dazzle prevention plate in response to an output signal from the control means.

4 Claims, 6 Drawing Sheets

U.S. PATENT DOCUMENTS

| | | | |
|---|---|---|---|
| 5,444,232 A | 8/1995 | Gunz et al. | 250/201.1 |
| 6,552,316 B1 | 4/2003 | Bae | 250/201.1 |
| 6,614,409 B1 | 9/2003 | Bae | 345/8 |

FOREIGN PATENT DOCUMENTS

WO     WO 02/49554 A1    6/2002

OTHER PUBLICATIONS

PCT International Search Report; International Application No. PCT/KR2005/000005; International filing date: Jan. 4, 2005; Date of Mailing: Apr. 27, 2005.

* cited by examiner

[Fig. 1]
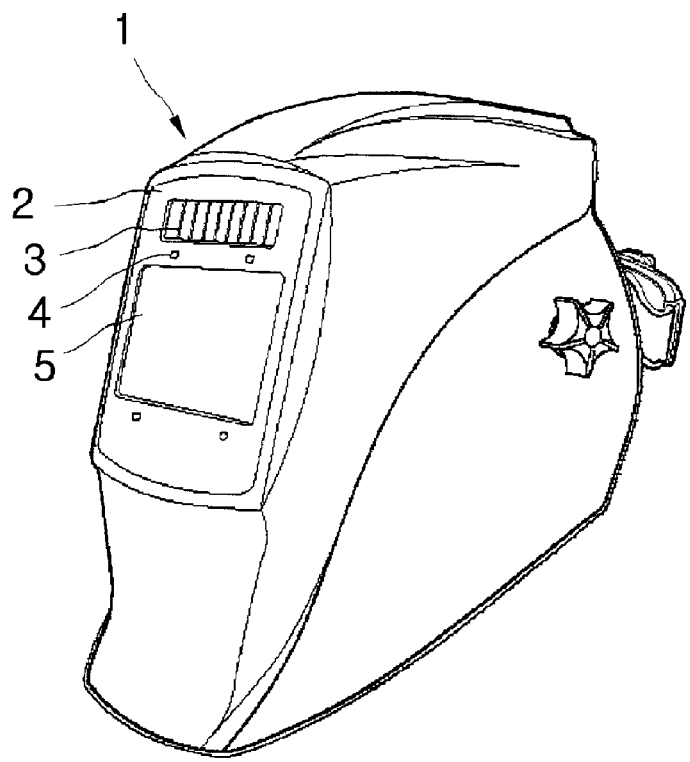
[Fig. 2]
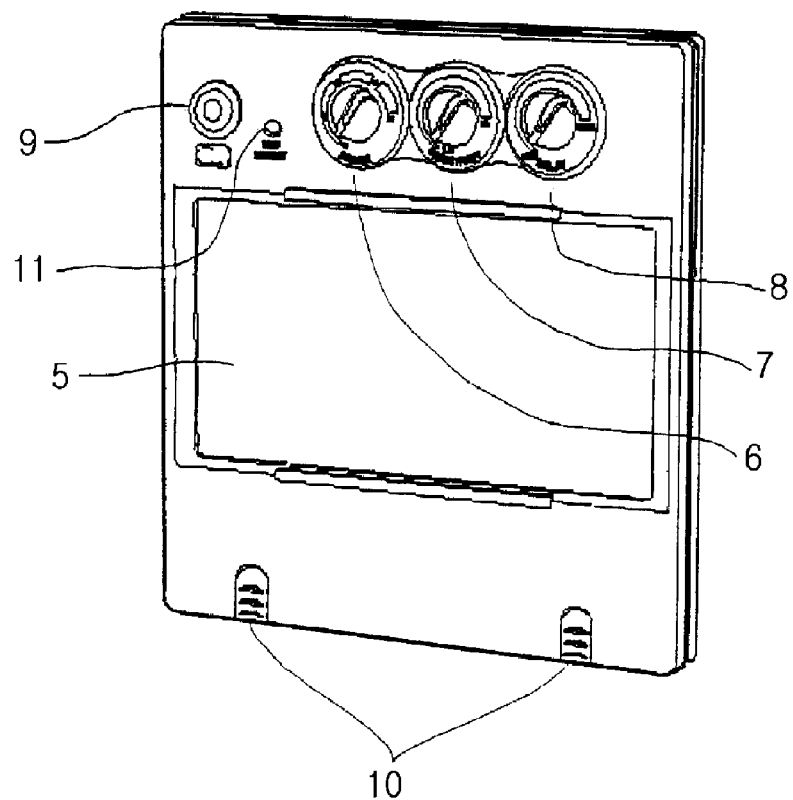

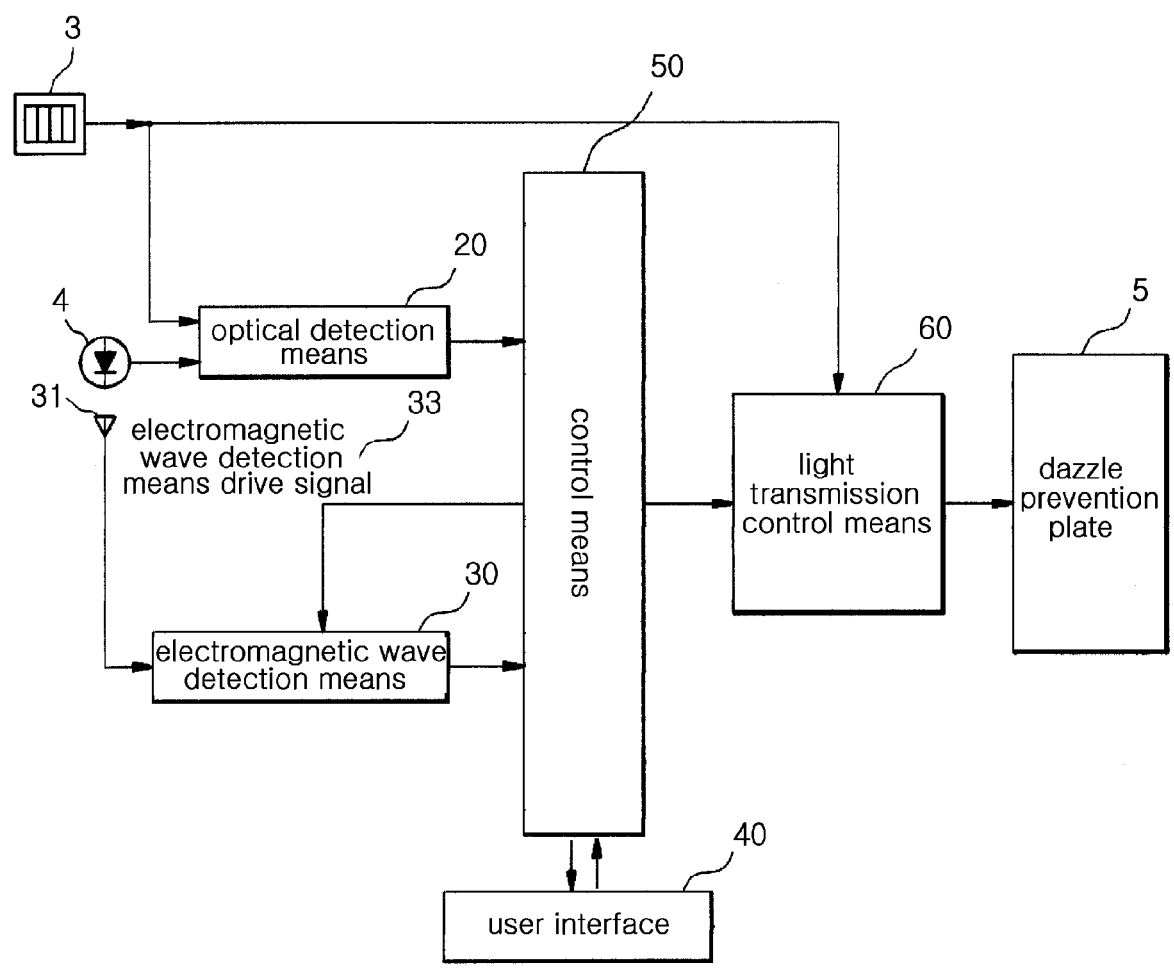
[Fig. 3]

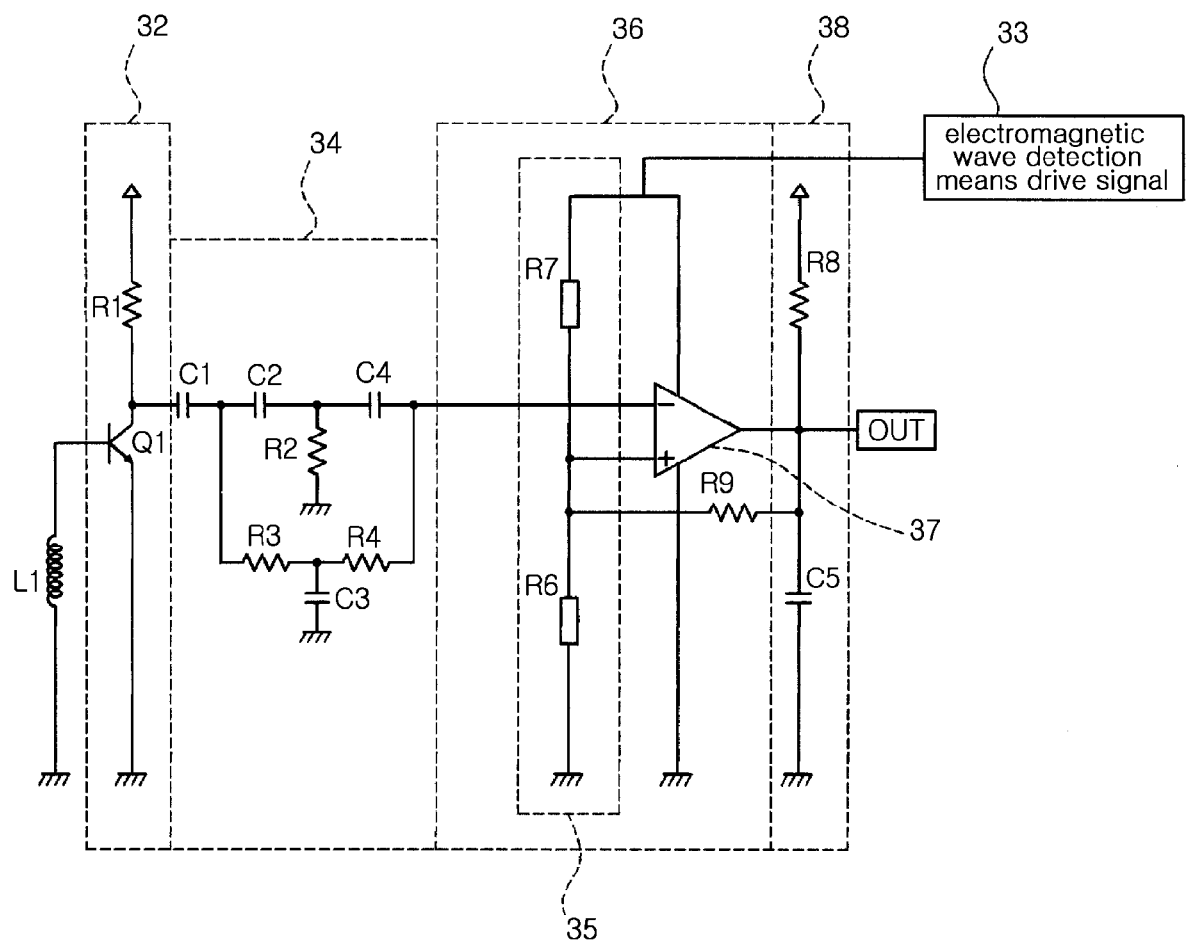
[Fig. 4]

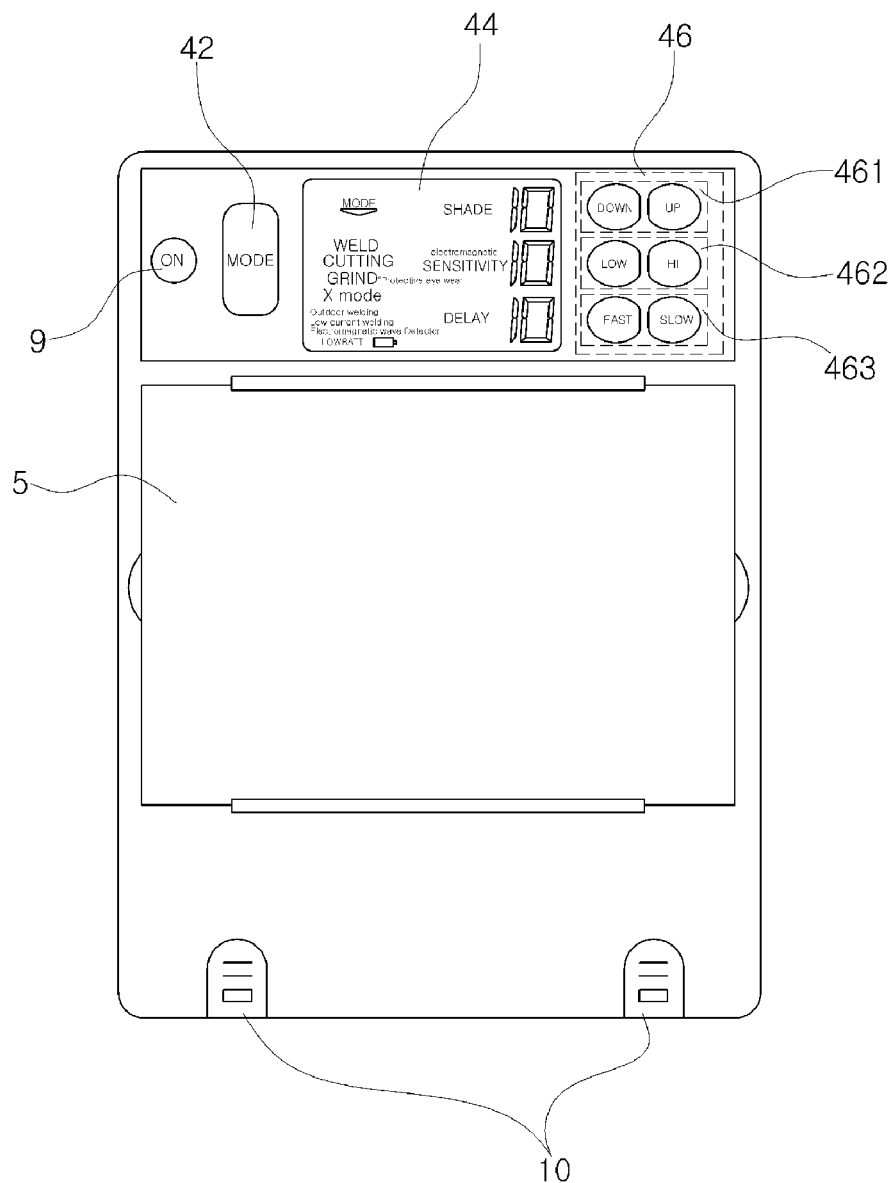
[Fig. 5]
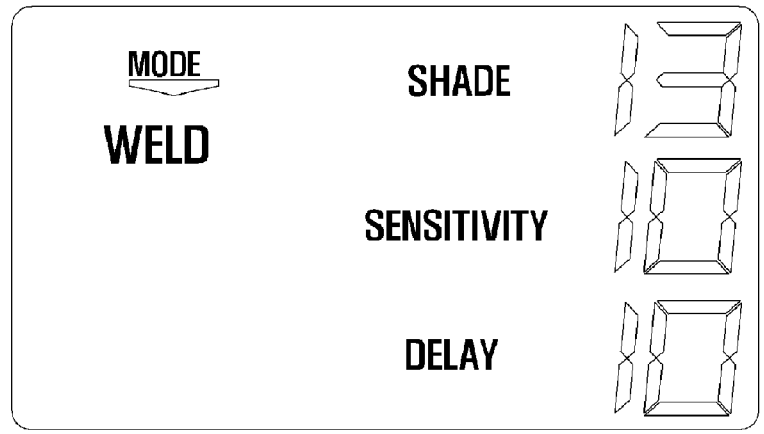
[Fig. 6]

[Fig. 7]
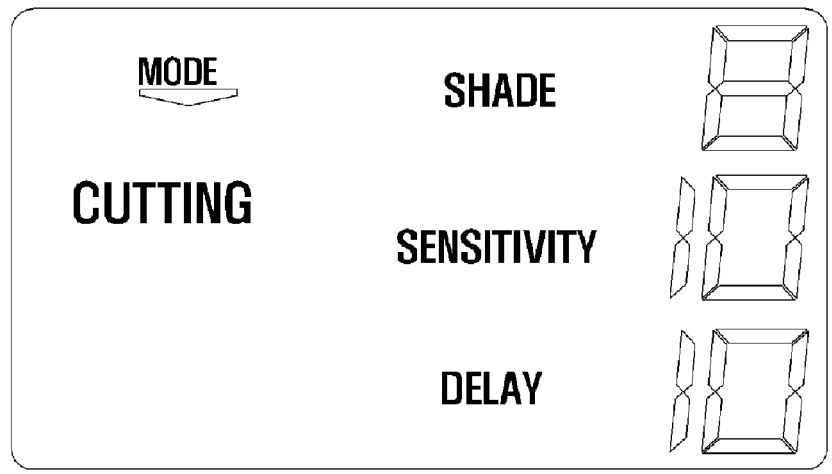
[Fig. 8]
[Fig. 9]
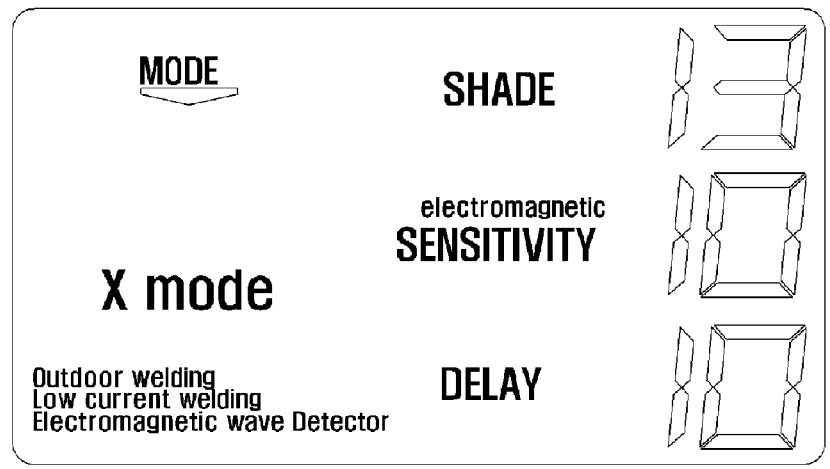

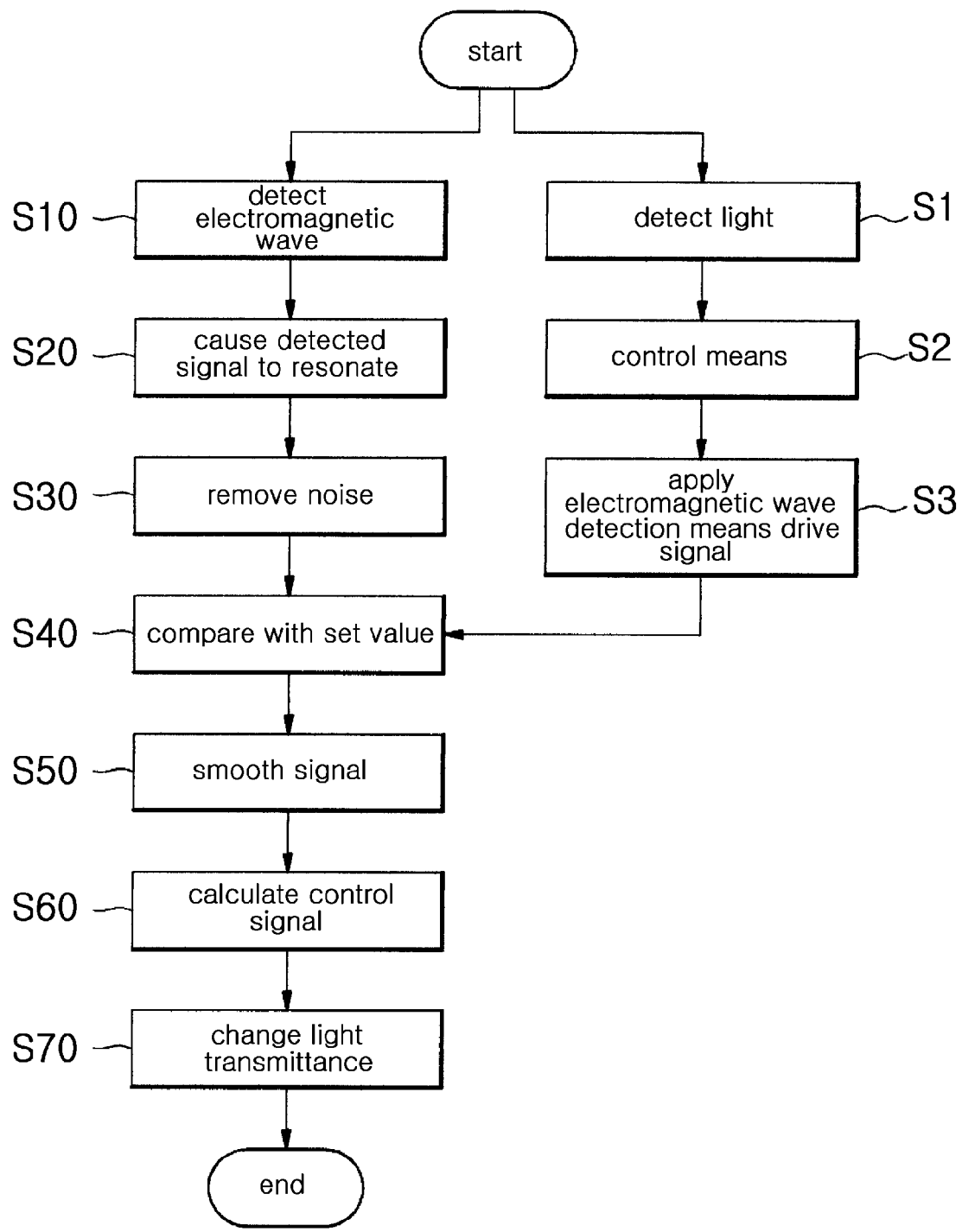
[Fig. 10]

DAZZLE PREVENTION DEVICE HAVING ELECTRO MAGNETIC WAVE DETECTION FUNCTION AND DETECTION MODE SELECTION

TECHNICAL FIELD

The present invention relates, in general, to a dazzle prevention device having an electromagnetic wave detection function and, more particularly, to an dazzle prevention device having an electromagnetic wave detection function, which detects an electromagnetic wave generated along with high illuminance light at the time of welding or cutting and protects the eyes of an operator from dazzle.

BACKGROUND ART

Conventionally, in order to control the transmittance of light generated from a welding or cutting torch, a dazzle prevention device, which is worn on the head of an operator and equipped with an optical detection means, has been used.

FIG. 1 is a perspective view showing a protective mask 1 equipped with a conventional dazzle prevention device 2.

As shown in FIG. 1, the protective mask 1 provided with the dazzle prevention device on the front of the protective mask 1 reduces the illuminance of light, which is applied to the eyes of an operator, through a dazzle prevention plate 5, that is, a Liquid Crystal Display (LCD) included in the dazzle prevention device 2.

In more detail, an optical detection means 4, such as a photodiode provided on the front of the dazzle prevention means 2 detects light generated from a welding or cutting torch, and a control circuit contained in the dazzle prevention device 2 performs control so that the dazzle prevention plate 5 is darkened to reduce the illuminance of light passing through the dazzle prevention plate, thus protecting the eyes of an operator.

FIG. 2 is a view showing a user interface for allowing a user to adjust the shading, light detection sensitivity and delay of the conventional dazzle prevention device 2.

Referring to FIG. 2, the user interface of the conventional dazzle prevention device 2 includes a shade adjusting means 6, a light detection sensitivity adjusting means 7, and a delay adjusting means 8.

The shade adjusting means 6 functions to adjust the shade number of the dazzle prevention plate 5. The shade number indicates the degree of darkness of the dazzle prevention plate 5. When the shade number is adjusted using the shade adjusting means 6, the transmissivity of the dazzle prevention plate 5 is adjusted.

The light detection sensitivity adjusting means 7 functions to adjust the light detection sensitivity of the dazzle prevention device 2. The light detection sensitivity is a numerical value that indicates the degree to which the control circuit responds to the output signal of the light sensor means 4. As the light detection sensitivity increases, the control circuit can respond better to the signal under low luminance.

The delay adjusting means 8 functions to adjust the delay of the dazzle prevention device 2. In the case where a delay number is low, the control circuit of the dazzle prevention device 2 switches the dazzle prevention plate 5 from a dark state to a light state when the light sensor means 4 detects the completion of welding work. In contrast, in the case where the delay number is high, a longer time is required for switching from a dark state to a light state.

Generally, in the dazzle prevention device-related field, 5~13 is used as the range of shade numbers, 0~10 is used as the range of light detection sensitivity numbers, and 0~10 is used as the range of delay numbers.

The user interface of the conventional dazzle prevention device 2 further includes a power switch 9 for selectively turning on and off power, a battery 10 for supplying power, and a low voltage indicator 11 for indicating the low voltage state of the device.

However, in the case where only the optical detection means is used erroneous operation has occurred frequently due to the difference between detected signals, which may occur according to the type of welding or welding machine, and coherent light.

That is, in the case where only the optical detection means is used the light detection sensitivity increases at the time of low current welding, outdoor welding and thin plate welding, in which case there occurs erroneous operation in that the dazzle prevention plate 5 does not lighten or lightens excessively slowly notwithstanding that the dazzle prevention plate 5 mist lighten in response to surrounding coherent light.

In order to prevent the above-described erroneous operation, a dazzle prevention device additionally equipped with an electromagnetic wave detection means is disclosed.

The conventional dazzle prevention device equipped with the electromagnetic wave detection means can effectively control the light transmittance of the dazzle prevention plate using an electromagnetic wave detection method during outdoor work exposed to sunbeams, during low current welding in which the illuminance of welding light is not significantly higher than illuminance of an environment, or in an environment in which it is difficult to identify welding light because the illuminance of the environment is high due to the use of a light having high directionality and high illuminance and thus, light other than the welding light is detected at the time of detecting light.

However, the conventional dazzle prevention device equipped with the electromagnetic wave detection means is disadvantageous in that it is set to use the electromagnetic wave detection method regardless of environmental conditions, so that in an environment where plenty of electromagnetic waves are generated the light transmittance of the dazzle prevention plate is unnecessarily lowered during work based on electromagnetic waves generated in the environment other than the welding or cutting torch of the operator, thus disturbing the precise operation of the operator.

Furthermore, in the conventional dazzle prevention device equipped with the electromagnetic wave detection means, electromagnetic wave detection sensitivity is fixed so that electromagnetic waves, which are generated by sources other than the machine of the operator, such as an electromagnetic wave generated by the machine of some other operator, can be detected thus resulting in erroneous operation.

Furthermore, the conventional dazzle prevention device equipped with the electromagnetic wave detection means is disadvantageous in that although the operator must precisely identify a welding or cutting area before starting work, an electromagnetic wave is generated prior to light at the time of applying power to a welding or cutting machine or turning on a welding or cutting start switch because the optical detection means and the electromagnetic wave detection means are constructed to independently operate, so that light transmittance is lowered based on a detected electromagnetic wave even though light is not generated thus hindering the operator from performing work after identifying a precise welding or cutting area.

DISCLOSURE OF INVENTION

Technical Problem

Accordingly, the present invention has been made keeping in mind the above problems occurring in the prior art, and an object of the present invention is to provide an dazzle prevention device having an electromagnetic wave detection function, which allows only an optical detection means or both the optical detection means and an electromagnetic wave detection means to be used according to environmental conditions, thus preventing the electromagnetic wave detection means from being used in the case where efficient control can be performed using only the optical detection means and the detection of an electromagnetic wave may cause erroneous operation.

Another object of the present invention is to provide an electromagnetic wave detection and dazzle prevention means, which detects only an electromagnetic wave, which is generated from the welding or cutting machine, using an electromagnetic wave sensor that is not affected much by the illuminance of an environment or the current of the welding machine and which is provided with an electromagnetic wave detection sensitivity adjustment means to prevent an electromagnetic wave generated from the environment from being detected.

A further object of the present invention is to provide an electromagnetic wave detection and dazzle prevention means that sets priority to allow an electromagnetic wave to be detected after a certain level of light has been detected from the welding or cutting torch of an operator, thus preventing the light transmittance of a dazzle prevention plate from being reduced before starting to detect light and allowing the operator to perform welding or cutting work after precisely identifying a welding or cutting area.

Technical Solution

In order to accomplish the above objects, the present invention provides an electromagnetic wave detection and dazzle prevention device for protecting eyes of an operator from light generated from a welding or cutting torch, including an optical detection means for detecting light generated from the welding or cutting torch; an electromagnetic wave sensor means for detecting an electromagnetic wave generated from the welding or cutting torch; an electromagnetic wave detection means for comparing a signal, which is input through the electromagnetic wave sensor means and resonated with a variably set reference value when an electromagnetic wave detection means drive signal is applied; a control means for, as the optical detection means starts to detect light, applying the electromagnetic wave detection mean drive signal to the electromagnetic wave detection means and monitoring the variation of an electromagnetic signal using the output of the electromagnetic wave detection means; and a light transmission control means for controlling the variation of light transmittance of the dazzle prevention plate in response to an output signal from the control means.

The device further includes a user interface that comprises a mode selection means capable of allowing the operator to select one from among a mode 1 using only the optical detection means and a mode 2 using both the optical detection means and the electromagnetic wave detection means, and display means capable of displaying a selected mode.

The control means can apply the electromagnetic wave detection means drive signal only when the made 2 is selected by the made selection means.

The electromagnetic wave detection means includes a resonance unit for allowing the electromagnetic wave, which is input through the electromagnetic wave sensor means, to resonate; a filter unit for removing noise from the output of the resonance unit; a comparison unit for comparing the output of the filter unit with the variably set reference value when the electromagnetic wave detection means drive signal is applied; and a time constant unit for smoothing the output of the comparison unit.

The comparison unit includes a comparator, in which the electromagnetic wave detection means drive signal is input to the power terminal thereof the output of the filter unit is input to the inverting input terminal thereof and a signal, into which the electromagnetic wave detection means drive signal is divided by a voltage divider including at least one variable resistor, is input to the non-inverting input terminal thereof.

The user interface further includes a digital adjustment means capable of varying a resistance value of the variable resistor.

The display means additionally displays an electromagnetic wave detection sensitivity number.

ADVANTAGEOUS EFFECTS

In accordance with the present invention, an electromagnetic wave detection and dazzle prevention device can determine the use of an electromagnetic wave detection means according to an environment, so that the electromagnetic wave detection means is not used when efficient control can be performed only by the optical detection means and the detection of an electromagnetic wave may cause erroneous operation, and the electromagnetic wave detection means can be additionally used according to the selection of the operator when efficient control cannot be performed only by the optical detection means, thus efficiently operating the dazzle prevention plate according to environmental conditions.

Furthermore, in accordance with the present invention, the electromagnetic detection sensitivity can be adjusted at the time of using the electromagnetic detection means, so that the detection of an electromagnetic wave generated in the environment of the operator can be minimized, thus preventing erroneous operation, such as an unnecessary reduction in light transmittance during work, and allowing the operator to perform precise operation.

Furthermore, the electromagnetic wave detection and dazzle prevention device can set priority so that an electromagnetic wave can be detected after light has been detected, so that the light transmittance of the dazzle prevention plate is reduced immediately after work has started thus allowing the operator to perform work after precisely identifying a welding or cutting area.

BRIEF DESCRIPTION OF THE DRAWINGS

FIG. 1 is a perspective view showing a protective mask equipped with a conventional dazzle prevention device;

FIG. 2 is a view showing a user interface for allowing a user to adjust the shading light detection sensitivity and delay of the conventional dazzle prevention device;

FIG. 3 is a block diagram showing a dazzle prevention device having an electromagnetic wave detection function according to the present invention;

FIG. 4 is a circuit diagram showing the electromagnetic wave detection means of the dazzle prevention device having an electromagnetic wave detection function according to the present invention;

FIG. 5 is a diagram showing an example of the user interface of the dazzle prevention device having an electromagnetic wave detection function according to the present invention;

FIGS. 6 to 9 are views showing the screens of modes 1A, 1B, 1C and 2 displayed on a display means; and FIG. 10 is a flowchart showing the operation of the dazzle prevention device having an electromagnetic wave detection function according to the present invention at the time when the mode 2 is selected.

BEST MODE FOR CARRYING OUT THE INVENTION

Reference should now be made to the drawings, in which the same reference numerals are used throughout the different drawings to designate the same or similar components.

With reference to the accompanying drawings, the construction and operation of the present invention are described in detail.

FIG. 3 is a block diagram showing an electromagnetic wave detection and dazzle prevention device according to the present invention. FIG. 4 is a circuit diagram showing the electromagnetic wave detection means 30 of the dazzle prevention device having an electromagnetic wave detection function according to the present invention.

As described in FIG. 3, the dazzle prevention device having an electromagnetic wave detection function according to the present invention includes an optical detection means 20, an electromagnetic wave detection means 30, a user interface 40, a control means 50 and a fight transmission control means 60.

The optical detection means 20 functions to detect light generated from a welding or cutting torch, and includes a filter and an amplifier. The optical detection means 20 detects the variation of light by comparing a signal from the optical detection means 4 with an output from a solar cell 3.

The electromagnetic wave detection means 30 functions to detect an electromagnetic wave generated from a welding or cutting torch. In the electromagnetic wave detection means 30, a signal, which is formed by an electromagnetic wave that is generated from the welding or cutting torch of the operator and input to the electromagnetic wave detection means 30, is resonated, filtered and then compared with a set value, so that an electromagnetic wave in a specific band is detected.

When an electromagnetic wave detection means drive signal 33 is applied the electromagnetic wave detection means 30 compares the output of a filter unit 34 with a variably set reference value. Power, which is formed by a resistor voltage divider, including at least one variable resistor that allows its resistance value to be varied by a variable volume, contact switch or digital adjustment means, is input to the non-inversion input terminal of a comparison unit 36, so that the reference value can be variably set.

FIG. 5 is a diagram showing an example of the user interface 40 of the dazzle prevention device having an electromagnetic wave detection function according to the present invention.

The user interface 40 functions to perform mode selection, mode indication, and the adjustment of shade, light detection sensitivity, delay and electromagnetic wave detection sensitivity.

Referring to FIG. 5, the user interface 40 includes a made selection means 42, a display means 44 and a digital adjustment means 46.

The mode selection means 42 allows a user to select one from among a mode 1 using only the optical detection means 20 and a mode 2 using both the optical detection means 20 and the electromagnetic wave made 30.

The display means 44 displays the mode selected by the user, a shade number, a light detection sensitivity number, a delay number and an electromagnetic detection sensitivity number on its LCD. In addition, the display means 44 displays a low voltage indication in the form of character and shape.

The digital adjustment means 46 functions to allow the user to adjust a shade number, a light detection sensitivity number, a delay number and an electromagnetic wave detection sensitivity number.

In detail, the digital adjustment means 46 is composed of a shade number adjustment button unit 461 capable of adjusting a shade number, a sensitivity number adjustment button unit 462 capable of adjusting light detection sensitivity and electromagnetic detection sensitivity, and a delay number adjustment button 463 capable of adjusting a delay number.

The button units 461 to 463 are each composed of a number increasing button and a number decreasing button. The two buttons are spaced apart from each other to increase the convenience of manipulation.

The sensitivity number adjustment button unit 462 is capable of adjusting a light detection sensitivity number in the mode 1, and is capable of adjusting an electromagnetic wave sensitivity number in the mode 2.

Meanwhile, the mode 1 using only the optical detection means 20 is divided into a mode 1A, a mode 1B and a mode 1C according to the type of welding work.

FIGS. 6 to 9 are views showing the screens of the modes 1A, 1B, 1C and 2 displayed on the display means 44.

Referring to FIG. 6, the mode 1A is a mode using a welding machine. When the user selects the mode 1A using the mode selection means 42, WELD is displayed on the display means 44. In the case of the mode 1A, the range of shade numbers that can be varied by the shade number adjustment button unit 461 is set to 9~13, the range of light detection sensitivity numbers that can be varied by the sensitivity number adjustment button unit 462 is set to 0~10, and the range of delay numbers that can be varied by the delay number adjustment button 463 is set to 0~10.

Referring to FIG. 7, the mode 1B is a mode using a cutting torch. When the user selects the mode 1B using the mode selection means 42, CUTTING is displayed on the display means 44. In the case of the mode 1B, the range of shade numbers that can be varied by the shade number adjustment button unit 461 is set to 5~8, the range of light detection sensitivity numbers that can be varied by the sensitivity number adjustment button unit 462 is set to 0~10, and the range of delay numbers that can be varied by the delay number adjustment button 463 is set to 0~10.

Referring to FIG. 8, the mode 1C is a mode using a grinder. When the user selects the mode 1C using the mode selection means 42, GRIND is displayed under cutting on the display means 44 and a guide message Protective eye wear, that is, a guide message instructing the user on the wearing of protective glasses, is input to a location beside GRIND. In the case of the mode 1C, the shade number of the dazzle prevention plate 5 is fixed to 4 regardless of a signal output from the optical detection means 20.

Referring to FIG. 9, when the user selects the mode 2, X mode is displayed under GRIND and guide messages Outdoor welding. Low current welding, and Electromagnetic wave detector are displayed below X mode. That is, a guide message instructing the user on the switching to and use of the made 2 at the time of outdoor welding low current welding and electromagnetic wave detection is output.

In the case of the mode 2, the range of shade numbers that can be varied by the shade number adjustment button unit 461 is set to 9~13, the range of light detection sensitivity numbers that can be varied by the sensitivity number adjustment button unit 462 is set to 0~10, and the range of delay numbers that can be varied by the delay number adjustment button 463 is set to 0~10.

That is, when the mode 2 is selected, the light detection sensitivity cannot be adjusted by the digital adjustment means 46, but only the electromagnetic wave sensitivity can be adjusted by the digital adjustment means 46.

The mode is changed from the mode 1A through the mode 1B and the mode 1C to the mode 2 whenever the mode selection means 42 is pressed.

The control means 50 is preferably a microcomputer or a control circuit including a microcomputer. When the mode 1 (one of the mode 1A to the mode 1C) is selected by the mode selection means 42, the electromagnetic wave detection means drive signal 33 is not applied and the light transmittance of the dazzle prevention plate can be controlled through light detection.

When the mode 2 is selected by the mode selection means 42, the optical detection means 20 starts to detect light and the output of the optical detection means 20 is input to the control means 50, the control means 50 applies the electromagnetic wave detection means drive signal 33 to the electromagnetic wave detection means 30 and determines priority to start to detect an input electromagnetic wave through the electromagnetic wave detection means 31. Additionally, the control means 50 monitors the variation of light input from the optical detection means 20 and the variation of an electromagnetic wave input from the electromagnetic wave detection means 30, and stops the operation of the device until the occurrence of the variation if the variation does not occur.

The light transmission control means 60 operates when power applied from the solar cell 3 exceeds a certain set value, and controls the light transmittance of the dazzle prevention plate 5 in response to the output signal of the control means 50.

Referring to FIG. 4, a preferred embodiment of the electromagnetic wave detection means 30 of the dazzle prevention means according to the present invention is described below.

As shown in FIG. 4, the electromagnetic wave detection means 30 includes a resonance unit 32, a filter unit 34, a comparison unit 36 and a time constant unit 38.

The resonance unit 32 includes an NPN type transistor Q1 which is switched by an electromagnetic wave applied to a base through the coil L1 of the electromagnetic wave sensor means 31 and in which power Vcc is applied to a collector through a resistor R1. Meanwhile, when an electromagnetic wave is detected through the coil L1, the emitter-base voltage of the transistor Q1 of the resonance unit 32 is made to resonate with the electromagnetic wave signal by the electromagnetic wave signal applied to the base, so that the transistor Q1 operates, thus generating a corresponding output through the collector.

The filter unit 34 is composed of condensers C1, C2 and C4 connected in series to the output of the collector of the transistor Q1, a resistor R2 connected to a ground between the condensers C2 and C4, resistors R3 and R4 connected in series to an end of the condenser C2 and an end of the condenser C4, and a condenser C3 connected to a ground between the resistors 16 and R4. Through the filter unit 34, noise is removed from an input signal.

The comparison unit 36 includes a comparator 37, in which the electromagnetic wave detection drive signal 33 is input to the power terminal thereof the output of the filter unit 34 is input to the inverting input terminal (−) thereof and a signal, into which the electromagnetic wave detection means drive signal 33 is divided by a voltage divider 35 including at least one variable resistor, is input to the non-inverting input terminal (+) thereof.

Since the electromagnetic wave detection means drive signal 33 is input to the power terminal of a comparator 37, the comparator 37 operates only when the electromagnetic detection signal 33 is input from the control means 50.

The output of the comparator 37 is fed back to the non-inverting input terminal (+) through the resistor R9, the comparator 37 compares a reference value set by a resistor voltage divider 35 and a signal input to the inverting input terminal (−).

The resistor voltage divider 35 is composed of two resistors R6 and R7. The electromagnetic wave detection means drive signal 33, which is applied on resistor R7, is divided at the ratio determined according to a voltage division rule, and a reference value, which is compared with the electromagnetic wave signal passed through the resonance unit 32 and the filter unit 34, is set for the contact between the two resistors R6 and R7.

At least one of the two resistors R6 and R7, which constitute the resistor voltage divider 35, is a variable resistor. The voltage input to the non-inverting input terminal (+) can be variably determined by adjusting the variable resistor and, thus, the reference value of the comparison unit 36 can be variably set, so that the operator can adjust the electromagnetic detection sensitivity. In this case, the magnitude of variable resistance is adjusted by the digital adjustment means 46. Besides the digital adjustment means 46, a variable volume or contact switch may be employed.

The time constant unit 38 is constructed so that the power Vcc is grounded through a resistor R8 and a condenser C5. The output of the comparison unit 36 is connected between the resistor R8 and the condenser C5, thus smoothing an output signal OUT.

The operation and effects of the dazzle prevention device having an electromagnetic wave detection function are described below.

When the operator selects the mode 1 using the mode selection means 42, the electromagnetic wave detection drive signal 33 is not applied from the control means 50, so that the light transmittance of the dazzle prevention plate 5 can be controlled only through light detection.

The operation and effects of the dazzle prevention device having an electromagnetic wave detection function according to the present invention at the time when the mode 2 is selected is described with reference to FIG. 10.

FIG. 10 is a flowchart showing the operation of the dazzle prevention device having an electromagnetic wave detection function according to the present invention at the time when the mode 2 is selected.

Referring to FIG. 10, the variation of light generated by a welding or cutting torch is detected by the optical detection means 20 at step S1. When a detection signal is input to the control means 50 at step S2, the electromagnetic wave detection means drive signal 33 is applied from the control means 50 to the electromagnetic wave detection means 30 at step S3, and the electromagnetic wave detection means 30 compares an electromagnetic wave signal input from the electromagnetic wave sensor means 31 with the set reference value at steps S10 to S40.

That is, the variation of the electromagnetic wave generated by the welding or cutting torch is applied to the coil L1 of the electromagnetic detection means 31 and detected at step S10. The impedance of the electromagnetic wave sensor means 31 is preferably designed so that an effective electromagnetic wave, which is desired to be detected in a welding environment, falls within a range of 2 KHz to 400 KHz.

The transistor Q1 of the resonance unit 32, in which an electromagnetic wave varying as described above is applied to the base, is repeatedly and alternately turned on and off according to the electric potential of base, so that the effective signal of an electromagnetic wave is output from the collector, to which power Vcc is applied through the resistor R1, by the resonance of the transistor Q1 at step S20.

The effective signal of the electromagnetic wave output by the resonance as described above becomes free from noise while passing through the filter unit 34 including the resistors R1, R3 and R4 and the condensers C1, C2, C3 and C4, finally, a signal having only an alternating component is output as an effective signal at step S30.

The signal, the noise of which is removed by the filter unit 34, is input to the inverting input terminal (−) of the comparator 37 that constitutes a part of the comparison unit 36.

In that case, the electromagnetic wave detection means drive signal 33, which is divided by the resistors R7 and R6 of the resistor voltage divider, is input to the non-inverting input terminal (+) of the comparator 37, and becomes a reference value that will be compared with a signal input from the filter unit 34.

Thereafter, the comparator 37 compares the signal output through the filter unit 34 with the reference value input to the non-inverting input terminal (+), and outputs a comparison signal at step S40. The comparator 37 has hysteresis characteristics due to a resistor R9 connected to the output and input of the comparator 37. Accordingly, the output voltage of the comparator 37 increases the electric potential of the non-inverting input terminal (+) through the resistor R9, so that operation insensitive to the noise signal input to the inverting input terminal (−) is performed.

The output signal OUT is smoothed by an integration circuit that is constituted by the resistor R8 and the condenser C5 of the time constant unit 38 at step S50.

The signal smoothed as described above is input to the control unit 50, and is calculated by the microcomputer or control circuit including a microcomputer to detect so that the amplitude of an electromagnetic wave can be detected at step S60.

In accordance with the result of the calculation at step S60, the control means 50 detects an electromagnetic wave, which is generated from the welding or cutting torch, to change the light transmittance of the dazzle prevention plate 5, so that operation is performed so that the electromagnetic wave as well as the light, which are generated in the welding environment, are detected and controlled thus protecting the eyes of the operator at step S70.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. An dazzle prevention device having an electromagnetic wave detection function, the device protecting eyes of an operator from light generated from a welding or cutting torch, comprising:

optical detection means for detecting light generated from the welding or cutting torch;

electromagnetic wave sensor means for detecting an electromagnetic wave generated from the welding or cutting torch;

electromagnetic wave detection means for comparing a signal, which is input through the electromagnetic wave sensor means and resonated with a variably set reference value when an electromagnetic wave detection means drive signal is applied;

control means for, as the optical detection means staffs to detect light, applying the electromagnetic wave detection means drive signal to the electromagnetic wave detection means and monitoring variation of an electromagnetic signal using an output of the electromagnetic wave detection means; and light transmission control means for controlling variation of light transmittance of a dazzle prevention plate in response to an output signal from the control means, wherein the electromagnetic wave detection means includes a user interface that comprises:

mode selection means capable of allowing the operator to select mode 1 using only the optical detection means or mode 2 using both the optical detection means and the electromagnetic wave detection means; and display means capable of displaying a selected mode.

2. The device according to claim 1, wherein the control means can apply the electromagnetic wave detection means drive signal only when the mode 2 is selected by the mode selection means.

3. The device according to claim 1, wherein the user interface further comprises digital adjustment means capable of varying a resistance value of a variable resistor.

4. The according to claim 3, wherein the display means additionally displays an electromagnetic wave detection sensitivity number.

* * * * *